United States Patent [19]

Sturm et al.

[11] Patent Number: 5,484,928
[45] Date of Patent: Jan. 16, 1996

[54] 2-(2-AMINOTHIAZOL-4-YL)-2-OXOACETIC ACID DERIVATIVES

[75] Inventors: Hubert Sturm, Landeck; Heinrich Thaler, Kirchbichl; Werner Veit, Kufstein, all of Austria

[73] Assignee: Biochemie Gesellschaft m.b.H., Tyrol, Austria

[21] Appl. No.: 55,613

[22] Filed: Apr. 30, 1993

Related U.S. Application Data

[63] Continuation of Ser. No. 764,579, Sep. 24, 1991, abandoned, which is a continuation of Ser. No. 519,991, Apr. 24, 1990, abandoned, which is a continuation of Ser. No. 445,319, Nov. 29, 1989, abandoned, which is a continuation of Ser. No. 382,142, Jun. 23, 1989, abandoned, which is a continuation of Ser. No. 296,554, Jan. 4, 1989, abandoned, which is a continuation of Ser. No. 197,921, May 24, 1988, abandoned, which is a continuation of Ser. No. 52,678, May 13, 1987, abandoned, which is a continuation of Ser. No. 815,093, Dec. 10, 1985, abandoned.

[30] Foreign Application Priority Data

Apr. 10, 1984 [AT] Austria .................................. 1197/84
Apr. 10, 1984 [AT] Austria .................................. 1198/84

[51] Int. Cl.⁶ .................................................. C07D 277/40
[52] U.S. Cl. ........................... 546/280; 548/152; 548/165
[58] Field of Search .............................. 540/225; 548/194, 548/152, 165; 546/280

[56] References Cited

U.S. PATENT DOCUMENTS

| | | | |
|---|---|---|---|
| 4,440,766 | 4/1984 | Kamiya et al. | 540/225 |
| 4,563,534 | 1/1986 | Sadaki et al. | 548/194 |
| 4,667,040 | 5/1987 | Sadaki et al. | 548/150 |
| 4,704,457 | 11/1987 | Moniot et al. | 540/225 |
| 4,727,154 | 2/1988 | Papenfuhs | 548/150 |
| 5,138,049 | 8/1992 | Asher et al. | 540/227 |

*Primary Examiner*—Nicholas Rizzo
*Attorney, Agent, or Firm*—Robert S. Honor; Melvyn M. Kassenoff; Thomas O. McGovern

[57] ABSTRACT

Compound of formula IVe

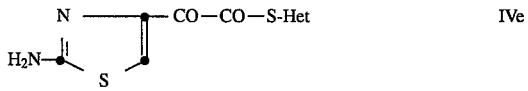

where Het is 2-pyridyl or 2-benzothiazolyl, are useful as acylating agents in preparing 7-[2-(2-amino-4-thiazol)-2-oxoacetyl]-cephalosporin intermediates.

2 Claims, No Drawings

2-(2-AMINOTHIAZOL-4-YL)-2-OXOACETIC ACID DERIVATIVES

This is a continuation of application Ser. No. 07/764,579, filed Sep. 24, 1991 now abandoned, which in turn is a continuation of application Ser. No. 07/519,991, filed Apr. 24, 1990, now abandoned, which in turn is a continuation of application Ser. No. 07/445,319, filed Nov. 29, 1989, now abandoned which in turn is a continuation of application Ser. No. 07/382,142, filed Jun. 23, 1989, now abandoned, which in turn is a continuation of application Ser. No. 07/296,554, filed Jan. 4, 1989 now abandoned, which in turn is a continuation of application Ser. No. 07/197,921, filed May 24, 1988, now abandoned, which in turn is a continuation of application Ser. No. 07/052,678, filed May 13, 1987 now abandoned, which in turn is a continuation of application Ser. No. 06/815,093, filed Dec. 10, 1985, now abandoned which is a 371 of PCT/EP85/00156.

The invention relates to a process for the production of cephalosporin intermediate products of formula

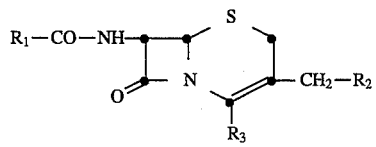

wherein $R_1$ denotes a group of formula

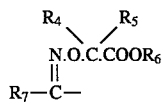

whereby $R_4$ and $R_5$ are the same or different and denote hydrogen or an optionally substituted lower alkyl group, $R_6$ signifies an ester-forming group and $R_7$ denotes a 5-membered, oxygen-, nitrogen- and/or sulphur-containing heterocycle which is optionally substituted by the azido or amino group, and the oximino group has syn-configuration, or $R_1$ denotes the group of formula

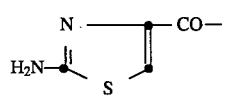

$R_2$ denotes hydrogen, the acetoxy, the carbamoyloxy, a S-Y- group, whereby Y signifies an unsubstituted or substituted heterocycle, or $R_2$ denotes an optionally substituted pyridinium of formula

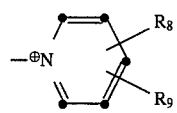

whereby $R_8$ and $R_9$ are the same or different and respectively denote hydrogen, halogen, alkyl, hydroxy, carboxamido, alkoxycarbonyl, amino, monoalkylamino or dialkylamino, or together signify an optionally substituted, 5- or 6-membered carbocyclic ring, and $R_3$ signifies the carboxyl, the carboxylate or a carboxylic acid ester group, and their use.

Furthermore, the invention also relates to the new cephalosporin intermediate products of formula

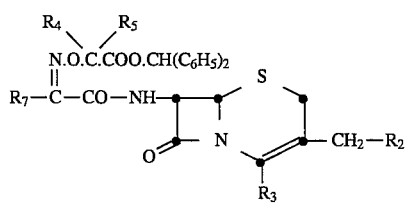

wherein $R_2$ to $R_5$ and $R_7$ are defined as above, as well as cephalosporin intermediate products of formula

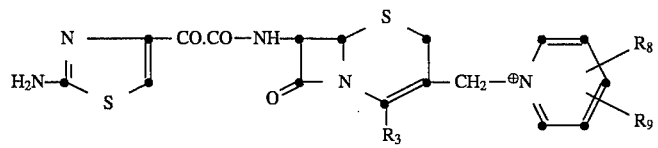

wherein $R_3$, $R_8$ and $R_9$ are defined as above.

Valuable cephalosporin antibiotics can be produced from the cephalosporin intermediate products of formula I. Compounds in which $R_1$ signifies a group of formula II are characterised by the presence of an oximino group in the 7-acylamido side chain bonded to the cephalosporin nucleus. This oximino group may exist in syn- or anti-configuration, whereby the compounds having syn-configuration are preferred.

As detailed, the heterocyclic ring in $R_7$ contains one or several oxygen, sulphur and/or nitrogen atoms as hetero atoms. However, it may additionally contain one or several nitrogen atoms. Suitable heterocycles are for example pyrazolyl, furyl, thienyl, thiazolyl, thiadiazolyl, oxazolyl and oxadiazolyl. The heterocycle may be unsubstituted or substituted by amino. The heterocycle of $R_7$ is preferably thiazolyl, preferably substituted by amino.

One preferable group of syn-isomers are compounds of formula

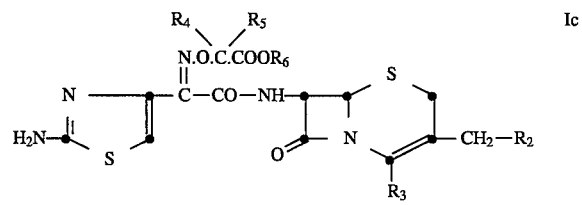

wherein $R_2$ to $R_6$ are defined as above.

In these compounds, $R_2$ may be hydrogen. It can also be carbamoyloxy. However, it preferably signifies acetoxy, -S-Y or optionally substituted pyridinium. Suitable heterocycles as Y are known. Preferred heterocycles are for example thiadiazolyl, diazolyl, triazolyl, tetrazolyl, thiazolyl, thiatriazolyl, oxazolyl, oxadiazolyl, triazolylpyridyl, purinyl, pyridyl, pyrimidinyl, pyridazinyl, pyrazolyl and triazinyl. These heterocycles may be unsubstituted or may be substituted for example up to three times. Suitable substituents are $(C_{1-4})$alkyl, $(C_{1-4})$alkoxy, halogen, trihalo-$(C_{1-4})$alkyl, hydroxy, oxo, mercapto, amino, carboxyl, carbamoyl, di-$(C_{1-4})$alkylamino, carboxymethyl, carbamoylmethyl, sulphomethyl and methoxycarbonylamino. Preferred heterocycles which have been previously described in literature include tetrazolyl, especially 1-methyl-1H-tetrazol-5-yl, and triazinyl, especially 1,2,5,6-tetrahydro-2-methyl-5,6-dioxo-as-triazin-3-yl, 2,5-dihydro-6-hydroxy-2-methyl-5-oxo-as-triazin-3-yl or 1,4,5,6-tetrahydro-4-methyl-5,6-dioxo-as-triazin-3-yl. $R_2$ is preferably acetoxy, 1-methyl-1H-tetrazol-5-ylthio, 2,5-dihydro-6-hydroxy-2-methyl-5-oxo-as-triazin-3-ylthio or pyridinium.

As is known in the field of cephalosporins, the compounds may exist in the form of free acids ($R_3$=COOH) or salts, for example alkali metal salts or alkaline earth metal salts, preferably alkali metal salts, such as sodium salts. Furthermore, the compounds may also exist in the form of esters, for example in the form of pivaloyloxymethylester, but also as other esters, for example acetoxymethyl-, 1-acetoxyethyl-, 1-ethoxycarbonyloxyethyl-, 5-indanoyl- or preferably hexanoylmethyl-, phthalidyl-, carbethoxymethoxymethyl- or 3-carbethoxy-1-acetonyl-esters. If $R_2$ denotes an optionally substituted pyridinium group, the compounds of formula I can also exist as inner salts. Further $R_2$ groups which contain basic radicals can similarly exist in the form of salts.

Especially preferred are syn-isomers of formula

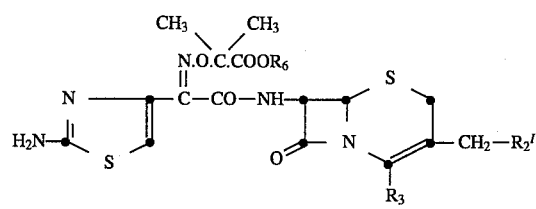

wherein $R_3$ and $R_6$ are defined as above, and $R_2^I$ signifies acetoxy or pyridinium, and their salts.

Most particularly preferred are compounds of formula

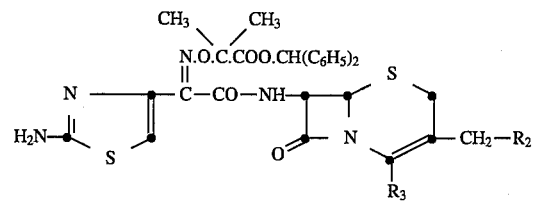

wherein $R_2$ and $R_3$ are defined as above, and their salts.

Also preferred are compounds of formula

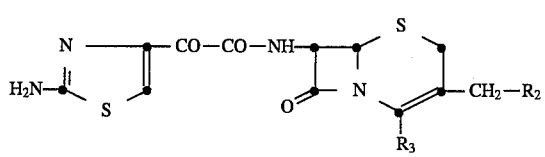

wherein $R_2$ and $R_3$ are defined as above.

As already mentioned, the cephalosporin antibiotics which can be produced from the compounds of formula I are known, and various methods for their preparation have already been proposed. One of these methods comprises the acylation of the corresponding, optionally protected 7-aminocephalosporanic acid derivative with an active derivative of an acid of formula $$R_1\text{—COOH} \qquad\qquad A$$

wherein $R_1$ is defined as above.

The various active derivatives which have been proposed also include active esters. In order to produce syn-isomers of the compounds of formula I, in which $R_1$ denotes a group of formula II, the active derivatives of the acid of formula A should similarly be present as syn-isomers in the purest possible form, and where possible, the syn-configuration should not be influenced by further reaction steps, and in particular not by the acylation step. Various active derivatives which have previously been proposed, especially active esters, have the disadvantage that the syn-configuration is unstable during preparation and use, whereupon the anti-isomer is increasingly formed and as a result of this the yield of the desired syn-isomer is reduced.

A further difficulty arising in the production of the preferred compounds of formulae Ic and If is that, in practice, the amino substituent in the thiazolyl ring of the side chain must be protected before activating the acid function, since otherwise competitive reactions may lead to great reductions in yield of the end product. However, the introduction of protecting groups before the acylation step and their subsequent splitting off usually leads to reduced yields and purity of the end product, and considerably increases the reaction time, energy, consumption and costs.

The present invention includes a process for the production of the desired compounds of formula I in high yield and purity. In particular, the syn-isomers of compounds of formula Ic and the compounds of formula If can be obtained in high yield and purity without having to protect the amino substituent in the thiazolyl ring of the side chain.

The present invention includes in particular a process for the production of compounds of formula I and their salts, characterised in that a compound of formula

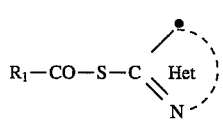

and/or

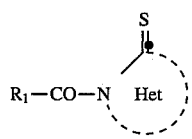

wherein $R_1$ is defined as above, and

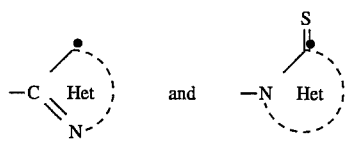

denote a 5- or 6-membered heterocycle, which in addition to the N-atom may contain one or two further hetero atoms, for example O, N and S and which may be substituted or anellated with an optionally substituted benzene ring, is reacted with a compound of formula

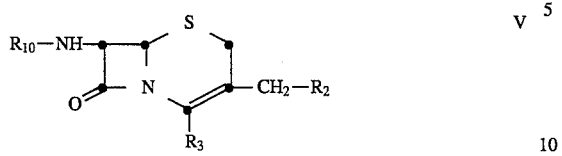

wherein $R_2$ and $R_3$ are defined as above, and $R_{10}$ denotes hydrogen or an amino protecting group, and if desired, an end product obtained is deprotected, and an end product obtained in which $R_3$ denotes COOH is optionally converted into a salt, or vice versa.

The compounds of formula IV may also be present in the form of formula IVa, whereby the relationship of the two forms to one another is dependent on the reaction components and the reaction conditions. If compounds having the structure of formula IV are indicated, these always also include compounds having the structure of formula IVa.

The process according to the invention is preferably effected in an inert solvent or in a mixture of such a solvent with water, e.g. in a chlorinated hydrocarbon such as dichloromethane, or in an acid ester such as ethyl acetate, or in acetone, dimethylformamide or dimethyl sulphoxide, at a temperature of $-40°$ to $+60°$ C., especially $-15°$ to $+25°$ C., and advantageously at $0°$ to $20°$ C. The duration of the reaction is approximately ½ to 48 hours. The reactants of formulae IV and V are either used in stoichio-metric quantities, or an excess of up to 25% of the compound of formula IV is used.

In the production of compounds of formula I in which $R_3$ signifies COOH, and their salts, the carboxyl group in the starting product of formula V can be protected. Suitable protecting groups are known and include not only those defined above, but also silylester protecting groups, especially the trimethylsilyl protecting group, which can be introduced e.g. by means of a reaction of the free acid with N,O-bis(trimethylsilyl)acetamide.

The 7-amino group of the starting material of formula V can similarly be protected. Suitable protecting groups are known and include e.g. the trimethylsilyl group, which can be introduced for example simultaneously with the protection of the carboxyl group.

If $R_1$ in the heterocycle includes an amino substituent, this amino substituent may be present in the starting material in free form or in protected form. As already mentioned, protection is generally not necessary. Should however protection be desired in spite of this, it may take place in known manner, using suitable known protecting groups.

After the reaction of the compounds of formulae IV and V, successive deprotection reactions can be effected in known manner. Similarly, conversion of the free acid form ($R_3$=COOH) into the salts can be effected by known methods.

The end products can be isolated and purified by known methods.

In the process according to the invention, heterocyclic thio-esters are used as the reactive derivative of the acid of formula A. It has surprisingly been found that these esters can be produced and used, whilst the -C=N-syn-configuration is practically wholly maintained. Furthermore, it has surprisingly been found that an amino group present in the heterocycle of these esters does not lead to self-reaction. As a result, protection of this amino group in the subsequent acylation is not necessary. On the other hand, the amino group can of course be protected if this is desirable for another reason.

In the compounds of formula IV, the type of the ring

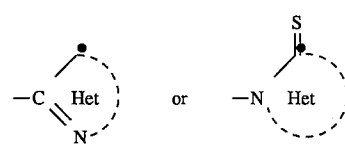

is not critical. The preferred compounds are determined by factors such as ease of production and availability of the starting material. The ring is preferably 2-pyridyl or in particular 2-benzothiazolyl. It may also be pyrimidinyl, triazolyl or thiazolyl. The preferred compounds of formula IV correspond to the preferred end products, namely the syn-isomers of formulae

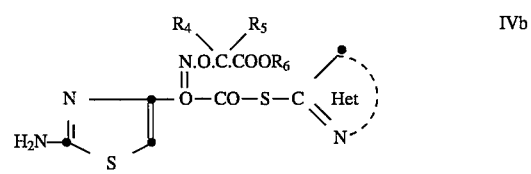

IVb

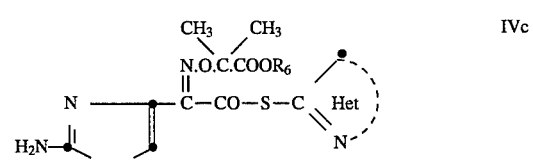

IVc and

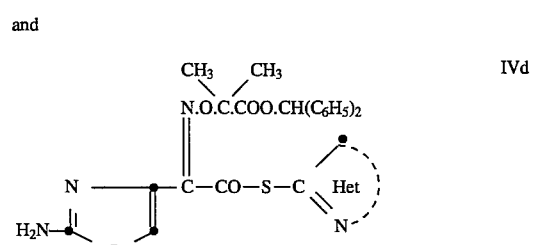

IVd as well as the compounds of formula

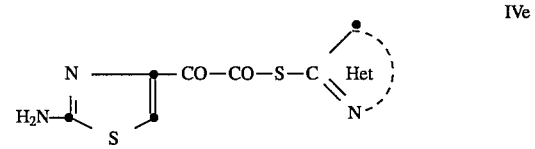

IVe wherein $R_4$ to $R_6$ and

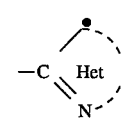

are defined as above.

The compounds of formula IV may be obtained by the esterification of compounds of formula $R_1$—COOH  VI wherein $R_1$ is defined as above.

Esterification may be effected for example by means of a reaction with a compound of formula

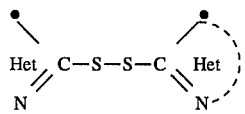   VII wherein both

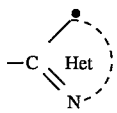

are the same and are defined as above.

This esterification is preferably effected in the presence of a tri(lower-alkyl)- or tri(aryl)-phosphine or -phosphite, especially triphenylphosphine, and preferably at a temperature of −30° to +50° C., especially −20° to +25° C., advantageously −5° to +5° C. The solvent employed is an inert organic solvent which does not contain hydroxyl groups, e.g. a chlorinated hydrocarbon such as dichloromethane. If a compound of formula IV is desired in which $R_1$ is a heterocycle with a protected amino group, the amino protecting group can be introduced before or after esterification. The end products can be crystallised by treatment with lower alcohols and purified, whereby care must be taken that the temperature does not exceed 20° C., preferably 0° C.

As already mentioned, the compounds of formula I are intermediate products in the production of known antibiotics. These exhibit inhibiting activiey against bacteria, as can be shown by examinations in vitro using the serial dilution test and in vivo by tests on mice, using various strains, e.g. of Staphylococcus aureus, Streptococcus pyogenes, Streptococcus faecalis, Escherichia coli, Proteus vulgaris, Proteus mirabilis, Proteus morganii, Shigella Dysenteria, Shigella sonnei, Shigella flexneri, Alcaligenes faecalis, Klebsiella aerogenes, Klebsiella pneunomiae, Serrata marcescens, Salmonella Heidelberg, Salmonella typhimurium, Salmonella enteritidis and Neisseria gonorrhoae. This inhibiting activity was established from a concentration of ca. 0.01 to 50 μg/ml, or resp. from a dosage of ca. 0.1 to 100 mg/kg body weight.

These cephalosporin antibiotics can therefore be used as antibacterially active antibiotics. For this application, the dosage to be administered depends on the compound used and the type of administration, as well as the type of treatment. Satisfactory results are obtained when administering a daily dosage of ca. 1 to 6 g. If necessary, this amount can be given in correspondingly smaller doses of 0.25 to 3 g two to four times daily, or in sustained release form.

The compounds in which $R_3$ denotes carboxyl can be used in the form of the free acids or their physiologically acceptable salts, whereby the salts have the same order of activity as the free acids. Suitable salt forms are for example alkali metal salts and alkaline earth metal salts, preferably alkali metal salts, especially sodium salts. The compounds can be administered together with inorganic or organic, pharmacologically inert diluents or carriers or adjuvants. They are employed for example as a constituent of capsules, injection or instillation preparations.

In the following examples which illustrate the invention more fully but in no way limit its scope, all temperatures are given in degrees celsius.

EXAMPLE 1

(6R,7R)-7-[[2-(2-amino-4-thiazolyl)-(Z)-2-(1-di-phenylmethoxycarbonyl-1-methylethoxy)imino]acetamido]-3-(1-pyridiniummethyl)ceph-3-em-4-carboxylic acid. Chloride 7 g of 2-(2-amino-4-thiazolyl-(Z)-2-[(1-diphenylmethoxycarbonyl-1-methylethoxy)imino]thioacetic acid-S-benzothiazol-2-ylester and 3.3 g of (6R,7R)-7-amino-3-(1-pyridiniummethyl)ceph-3-em-4-carboxylic acid chloride are stirred for 3 hours at room temperature in 50 ml of dichloromethane and 50 ml of methanol. The reaction mixture is concentrated by evaporation, and the oily residue is ground with 50 ml of acetone. The deposit is filtered off, washed with acetone and dried. 5.5 g of the title compound are obtained as a slightly yellow-coloured product. M.p.: from 170° (decomp.).

EXAMPLE 2

(6R,7R)-7-[[2-(2-amino-4-thiazolyl)-(Z)-2-(1-diphenylmethoxycarbonyl-1-methylethoxy)imino]acetamido]-3-(1-pyridiniummethyl)ceph-3-em-4-carboxylic acid. Chloride. Hydrochloride A solution of 7 ml of triethylamine in 20 ml of dichloromethane is added evenly over the course of 8 hours, whilst cooling with ice, to a mixture of 7 g of 2-(2-amino-4-thiazolyl)-(Z)-2-[(1-diphenylmethoxycarbonyl-1-methylethoxy)imino]thioacetic acid-S-benzothiazol-2-ylester and 3.3 g of (6R,7R)-7-amino-3-(1-pyridiniummethyl)ceph-3-em-4-carboxylic acid. chloride in 40 ml of dichloromethane, and stirring is effected for a further 12 hours at 0°. The reaction mixture is added to a 50° solution of 4.5 ml of concentrated hydrochloric acid in 500 ml of iso-propanol, whereby the title compound precipitates. It is cooled and stirred for one hour at 0°. The deposit is filtered off, washed with isopropanol and dried. 6 g of the title compound are obtained as a slightly yellow-coloured product. M.p.: from 160° (decomp.).

EXAMPLE 3

(6R,7R)-7-[[2-(2-amino-4-thiazolyl)-(Z)-2-(1-di-phenylmethoxycarbonyl-1-methylethoxy)imino]acetamido]-3-(1-pyridiniummethyl)ceph-3-em-4-carboxylic acid. Chloride. Hydrochloride 4.7 g of bis-(benzothiazol-2-yl)disulphide are added to 5 g of 2-(2-amino-4-thiazolyl)-(Z) -2-[(1-diphenylmethoxycarbonyl-1-methylethoxy)imino]acetic acid and 3.7 g of triphenylphosphine in 40 ml of dichloromethane, and stirring is effected for ½ hour at 0°. After adding 3.3 g of (6R,7R)-7-amino-3-(1-pyridiniummethyl)ceph-3-em-4-carboxylic acid. chloride, a solution of 7 ml of triethylamine in 20 ml of dichloromethane is added in drops at 0° over the course of 8 hours, whilst continuing to stir. Stirring continues for 12 hours at 0°, and working up takes place as described in example 2. 6 g of the title compound are obtained as an almost white product. M.p.: from 160° (decomp.).

$^1$H-NMR (90 MHz; DMSO-$d_6$): 9.84 (1H, d, —N—H—, J=8 Hz); 9.20, 8.67 and 8.23 (5H, pyridinium-H); 7.28 (10H, phenyl-H); 6.98 (1H, S, thiazolyl-H); 6.79 (1H, S, CH—Ph$_2$); 5.95 (1H, dd, H$_7$, J=8 Hz, J=5 Hz); 5.72 (2H, =C—C$\underline{H}_2$-pyridine); 5.27 (1H, d, H$_6$, J=5 Hz); 3.57 (2H, H$_2$ and H$_2$'); 1.63 (6H, C(C$\underline{H}_3$)$_2$).

EXAMPLE 4

(6R,7R)-7-[[2-(2-amino-4-thiazolyl)-(Z)-2-(1-di-phenylmethoxycarbonyl-1-methylethoxy)imino] acetamido]-3-(1-pyridiniummethyl)ceph-3-em-4-carboxylate:

5.1 g of (6R,7R)-7-amino-3-(1-pyridiniummethyl)ceph-3-em-4-carboxylic acid. chloride, 9.9 g of 2-(2-amino-4-thiazolyl)-(Z)-2-[(1-diphenylmethoxycarbonyl-1-methylethoxy)imino] thioacetic-acid-S-benzothiazol-2-ylester and 4.5 ml of tributylamine are added at −10° over the course of 30 minutes to a solvent mixture consisting of 10 ml of dimethyl sulphoxide and 7.5 ml of dimethylformamide. The resultant reaction solution is diluted with 10 ml of dimethylformamide and subsequently stirred for 5 hours at −10° to −5° and the product crystallises out. The reaction mixture is diluted with 50 ml of acetone, the product is separated and washed with acetone and vacuum dried. 10.6 g of the title compound are obtained as a white solvate (solvate with DMF and DMSO 1:1:1). M.p.: 160° (decomp.).

$^1$H-NMR (90 MHz; CD$_3$O): 9.21, 8.11 and 7.98 (5H, pyridinium-$\underline{H}$); 7.26 (10H, Ph—$\underline{H}$); 6.81, 6.75 (2H, 2s, C$\underline{H}$—Ph$_2$, thiazolyl-$\underline{H}$); 5.88 (1H, d, H$_7$, J=5 Hz); 5.69 and 5.33 (2H, =C—C$\underline{H}_2$-pyridine); 5.10 (1H, d, H$_6$, J=5 Hz); 3.60 and 3.07 (2H, 2d, H$_2$ and H$_2$', J=18 Hz); 1.59 (6H, s, C(C$\underline{H}_3$)$_2$).

EXAMPLE 5

(6R,7R)-7-[[2-(2-amino-4-thiazolyl)-(Z)-2-(1-diphenylmethoxycarbonyl-1-methylethoxy)imino] acetamido]-3-(1-pyridiniummethyl)ceph-3-em-4-carboxylic acid. Chloride 3.28 g of (6R,7R)-7-amino-3-(1-pyridiniummethyl)ceph-3-em-4-carboxylic acid. chloride and 3 ml of bis-(trimethylsilyl)acetamide are added at room temperature to a solvent mixture consisting of 10 ml of dichloromethane and 3 ml of dimethyl sulphoxide. Stirring is effected for 10 minutes at room temperature, whereby a clear solution results. The preparation is cooled to 0°, and 6 ml of 2N N,N-dimethylaniline. hydrochlorid solution in dichloromethane are added. Then, 6.5 g of 2-(2 -amino-4-thiazolyl)-(Z)-2-[(1-diphenylmethoxycarbonyl-1-methylethoxy) imino]thioacetic-acid-S-benzothiazol-2-ylester are added, and stirred for 12 hours at 0°. The reaction mixture is added to 100 ml of ethanol and left to stand for 5 hours at room temperature. The crystalline title compound is filtered off by suction, washed with a little cold ethanol and ether, and vacuum dried over phosphorus pentoxide. Yield: 6.29 g. M.p.: from 170° (decomp.).

EXAMPLE 6

(6R,7R)-3-acetoxymethyl-7-[[2-(2-amino-4-thiazolyl)-(Z)-2-(1-diphenylmethoxycarbonyl-1-methylethoxy)imino] acetamido]-ceph-3-em-4-carboxylic acid:

2.7 g of 3-acetoxymethyl-7-amino-3-cephem-4-carboxylic acid (7-ACA are stirred at room temperature in 12 ml of dichloromethane with 2.5 ml of bis-(trimethylsilyl)acetamide; within one hour, the 7-ACA goes into solution. Then, 6.5 g of 2-(2-amino-4-thiazolyl)-(Z)-2-[(1-diphenyl-methoxycarbonyl-1-methylethoxy)imino] thio-acetic-acid-S-benzothiazol-2-ylester are added. Stirring is effected for 3 hours at room temperature, and then the solvent is distilled off. The product is isolated from the residue by digesting with isopropanol. 5 g of the title compound are obtained as a white powder. M.p.: from 200° (decomp.).

H$^1$-NMR (90 MHz, DMSO-d$_6$): 9.49 (1H, d, J=9 Hz, amide); 7.33 (10H, m, phenyl); 6.82 (1H, s, thiazole); 6.71 (1H, s, Ph$_2$C$\underline{H}$); 5.88 (1H, dd, J=9 Hz, J=5 Hz, H$_7$); 5.20 (1H, d, J=5 Hz, H$_6$ 4.86 (2H, AB-q, J=13.5 HZ, CH$_2$O); 3.55 (2H, AB-q, J=18 Hz, S—C$\underline{H}_2$); 2.02 (3H, s, COC$\underline{H}_3$); 1.52 (6H, s, C(C$\underline{H}_3$)$_2$.

EXAMPLE 7

(6R,7R)-7-[[2-(2-amino-4-thiazolyl)-(Z)-2-(1-diphenylmethoxycarbonyl-1-methylethoxy)imino] acetamido]-3-[(2,3-cyclopeno-1-pyridinium)methyl]-3-cephem-4-carboxylate 3.7 g of 2-(2-amino-4-thiazolyl)-(Z)-2-[(diphenylmethoxycarbonyl- 1-methylethoxy)imino]thioacetic-acid-S-benzothiazol-2-ylester, 2 g of 7-amino-[(2,3-cyclopenteno-1-pyridinium)methyl]-3-cephem-4-carboxylic acid. chloride and 0.8 ml of triethylamine in 15 ml of dichloromethane are stirred for 12 hours at 0°. The mixture is then concentrated by evaporation under vacuum until dry, the residue is rubbed with acetone and filtered off. 2.4 g of the title compound are obtained as a light yellow powder. M.p.: from 140° (decomp.).

H$^1$-NMR (90 MHz, DMSO-d$_6$): 9.45 (1H, d, J=8 Hz, amide); 7.90, 8.38 and 9.15 (3H, pyridine); 7.33 (10H, m, phenyl); 6.80 (1H, s, thiazole); 6.65 (1H, s, Ph$_2$C$\underline{H}$); 5.80 (1H, dd, J=8 Hz, J= 5 Hz, H$_7$); 5.44 (2H, C$\underline{H}_2$—N); 5.13 (1H, d, J=5 Hz, H$_6$); 3.40 (2H, S—C$\underline{H}_2$); 3.12 (4H, cyclopentene); 2.18 (2H, m, cyclopentene); 1.50 (6H, s, C(C$\underline{H}_3$)$_2$).

EXAMPLE 8

(6R,7R)-7-[[2-(2-amino-4-thiazolyl)-(Z)-2-(1-diphenylmethoxycarbonyl-1-methylethoxy)imino]acetamido]-3-[(3-methyl-1-pyridinium)methyl]3-cephera-4-carboxylate 2.8 g of (6R,7R)-7-amino-3-[(3-methyl-1-pyridinium)methyl]-3 -cephem-4-carboxylic acid. iodide, 4.4 g of 2-(2-amino-4-thiazolyl)-(Z)-2-[(1-diphenylmethoxycarbonyl-1-methylethoxy)imino]thio-acetic acid-S-benzothiazol-2-ylester and 0.9 ml of triethylamine are stirred for 12 hours at 0° in 15 ml of dichloromethane. The mixture is then concentrated by evaporation under vacuum until dry, the residue is mixed with acetone and filtered off. 3.8 g of the title compound are obtained as a light yellow powder. M.p.: from 160° (decomp.).

H$^1$-NMR (90 MHz, DMSO-d$_6$/D$_2$O): 9.08, 8.40 and 8.00 (3H, picoline ring-H); 7.36 (10H, m, phenyl); 6.78 (1H, s, thiazole); 6.71 (1H, s, Ph$_2$C$\underline{H}$); 5.80 (1H, d, J=5 Hz, H$_7$); 5.54 (2H, CH$_2$—N); 5.13 (1H, d, J=5 Hz, H$_6$); 3.11 (2H, S—C$\underline{H}_2$); 2.51 (3H, s, picoline-C$\underline{H}_3$); 1.54 (6H, s, C(CH$_3$)$_2$).

EXAMPLE 9

(6R,7R)-7-[[2-(2-amino-4-thiazolyl)-(Z)-2-(1-diphenylmethoxycarbonyl-1-1-methylethoxy)imino] acetamido]-3-methyl-3-cephem-4-carboxylic acid. Hydrochloride 21.4 g of 7-amino-3-methyl-3-cephem-4-carboxylic acid (7-ADCA) are silylated at room temperature with 25 ml of bis-(trimethylsilyl)acetamide in 120 ml of dichloromethane. After adding 70.6 g of 2-(2-amino-4-thiazolyl)-(Z)-2-[(1-diphenylmethoxycarbonyl-1-methylethoxy)imino]thioacetic-acid-S-benzothiazol-2-ylester, the mixture is stirred for 3 hours and then concentrated by evaporation under vacuum until dry. The residue is dissolved in 500 ml of methanol and the title compound is precipitated with 100 ml of 1N hydrochloric acid. Yield: 39 g. M.p.: from 175° (decomp.).

H$^1$-NMR (90 MHz, DMSO-d$_6$): 9.71 (2H, d, J=8 Hz, amide); 7.44 (10H, m, phenyl); 7.04 (1H, s, thiazole); 6.82 (1H, s, Ph$_2$C$\underline{H}$); 5.76 (1H, dd, J=8 Hz, J=5 Hz, H$_7$); 5.17 (1H, d, J=5 Hz, H$_6$); 3.47 (2H, AB, S—C$\underline{H}_2$); 2.04 (3H, s, 3-CH$_3$); 1.62 (6H, s, C(C$\underline{H}_3$)$_2$).

EXAMPLE 10

(6R,7R)-7-[[2-(2-amino-4-thiazolyl)-(Z)-2-(1-diphenylmethoxycarbonyl-1-methylethoxy)imino]acetamido]-3-[[(1-methyl-1H-5-tetrazolyl)thio] -methyl]-3-cephem-4-carboxylic acid.

4.7 ml of N,O-bis-(trimethylsilyl)acetamide are added whilst cooling with water (<20°) to a suspension of 5.3 g of 7-amino-3-[[(1-methyl-1H-5-tetrazolyl)thio]-methyl]-3-cephem-4-carboxylic acid in 30 ml of dichloromethane. Stirring is effected at room temperature until a complete solution is formed, and the mixture is then cooled to 0°. After adding 11.8 g of 2-(2-amino-4 -thiazolyl)-(Z)-2-[(1-diphenylmethoxycarbonyl-1-methylethoxy)imino]thioacetic-acid-S-benzothiazol-2-ylester, stirring is effected for 12 hours at 0°. The reaction mixture is stirred into isopropanol, the deposit filtered off, washed and dried. 10.4 g of the title compound are obtained as a slightly yellow-coloured product. M.p.: 148°–150°.

H$^1$-NMR (90 MHz, DMSO-d$_6$): 9.52 (1H, d, —N—$\underline{H}$, J=8 Hz); 7.28 10H, m, phenyl-$\underline{H}$); 6.78 (1H, s, thiazolyl-$\underline{H}$); 6.71 (1H, s, Ph$_2$C$\underline{H}$); 5.85 (1H, dd, H$_7$, J=8 Hz, J=5 Hz); 5.14 (1H, d, H$_6$, J=5 Hz); 4.31 (2H, m, C$_3$—C$\underline{H}_2$—S); 3.94 (3H, s, N—C$\underline{H}_3$); 3.70 (2H, m, H$_2$ and H$_2$'); 1.57 (6H, s, C(C$\underline{H}_3$)$_2$).

EXAMPLE 11

(6R,7R)-7-[[2-(2-amino-4-thiazolyl)-(Z)-2-(1 -t-butoxycarbonyl-1-methylethoxy)imino]acetamido]-3-(1-pyridiniummethyl)-3-cephem-4-carboxylate 1.65 g of 2-(2-amino-4-thiazolyl)-(Z)-2-[(1 -t-butoxycarbonyl-1-methylethoxy)imino]acetic acid are reacted with 2.5 g of bis-(benzothiazol-2-y)disulphide and 1.9 g of triphenylphosphine in 20 ml of dichloromethane at 0° to form the activated thio-ester. After adding 1.6 g of (6R,7R)-7-amino-3-(1-pyridiniummethyl)-3-cephem-4-carboxylic acid. chloride and 0.75 ml of triethylamine, stirring is effected for 12 hours at 0°. The reaction mixture is then concentrated by evaporation under vacuum until dry the residue is mixed with acetone and filtered off. 1.4 g of the title compound are obtained as a light brown powder. M.p.: from 135° (decomp.).

H$^1$-NMR (90 MHz, DMSO-d$_6$/D$_2$O/DCl): 8.16 to 9.0 (5H, pyridinium); 7.15 (1H, s, thiazole); 5.92 (1H, d, J=5 Hz, H$_7$); 5.6 (2H, C$\underline{H}_2$—N); 5.32 (1H, d, J=5 Hz, H$_6$); 3.6 (2H, S—C$\underline{H}_2$); 1.54 (6H, s, C(CH$_3$)$_2$)$_2$); 1.45 (9H, s, C (CH$_3$)$_3$).

EXAMPLE 12

(6R,7R)-7-[[2-amino-4-thiazolyl)-(Z)-2-(diphenylmethoxycarbonylmethoxy)imino] acetamido]-3-(1-pyridiniummethyl)-3-cephem-4-carboxylate 2 g of 2-(2-amino-4-thiazolyl)-(Z)-2-[ (diphenylmethoxycarbonylmethoxy)imino]acetic acid are reacted with 2.2 g of bis-(benzothiazol-2-yl)disulphide and 1.7 g of triphenylphosphine in 20 ml of dichloromethane at 0° to form the activated thioester. After adding 1.5 g of (6R,7R)-7-amino-3-(1-pyridiniummethyl)-3-cephem-4-carboxylic acid. chloride and 0.7 ml of triethylamine, stirring is effected for 12 hours at 0°. The mixture is then concentrated by evaporation under vacuum until dry, the residue rubbed with acetone and filtered off. 3.1 g of the title compound are obtained as a light yellow powder. M.p.: from 140° (decomp.).

H$^1$-NMR (90 MHz; DMSO-d$_6$): 9.20, 8.65 and 8.20 (5H, pyridinium); 7.30 (10H, phenyl); 6.92 (1H, s, thiazole); 6.80 (1H, s, Ph$_2$C$\underline{H}$); 5.83 (1H, H$_7$); 5.62 (2H, C$\underline{H}_2$—N); 5.17 (1H, d, J=5 Hz, H$_6$); 4.88 (2H, O—C$\underline{H}_2$) ; 3.60 (2H, H$_2$ and H$_2$').

EXAMPLE 13

(6R,7R)-7-[[2-(2-amino-4-thiazolyl)-(Z)-2-(1 -diphenylmethoxycarbonylpropoxy)imino]acetamido]-3-(1-pyridiniummethyl)-3 -cephem-4-carboxylate 6 g of 2-(2-amino-4-thiazolyl)-(Z)-2-[(1 -diphenylmethoxycarbonylpropoxy)imino]acetic acid are reacted with 4.5 g of bis-(benzothiazol-2-yl)disulphide and 3.6 g of triphenylphosphine in 50 ml of dichloromethane to form the activated thioester. After adding 2.6 of (6R,7-amino-3-(1-pyridiniummethyl- 3-cephem-4 -carboxylic acid. chloride and 1 ml of triethylamine, stirring is effected for 12 hours at 0°. The reaction mixture is then concentrated by evaporation under vacuum until dry, the residue mixed with acetone and filtered off. 4.3 g of the title compound are obtained as a light yellow powder.

H$^1$-NMR (90 MHz, CD$_3$OD): 9.04, 8.58 and 8.10 (5H, pyridinium); 7.26 (10H, phenyl); 7.13 (1H, thiazole); 6.87 (1H, Ph$_2$C$\underline{H}$); 5.98 (1H, H$_7$); 5.62 (2H, C$\underline{H}_2$N); 5.38 (1H, H$_6$); 5.05 (1H, O—C$\underline{H}$—CH$_2$—); 3.70 (2H, S—C$\underline{H}_2$); 2.20 (2H, CH—C$\underline{H}_2$—CH$_3$); 1.0 (3H, —CH$_2$—C$\underline{H}_3$).

EXAMPLE 14

(6R,7R)-7-[[(Z)-2-(ethoxycarbonylmethoxy)imino-2 -(1H-pyrazol-3-yl]acetamido]-3-(1-pyridiniummethyl) ceph-3-em-4-carboxylate:

2.4 g of (Z)-2-[(ethoxycarbonylmethoxy)imino]-2-(1H-pyrazol-3 -yl)thioacetic-acid-S-benzothiazol-2-ylester are added at 0° to 1.6 g of (6R,7R)-7-amino-3-(1-pyridiniummethyl)ceph-3-em-4-carboxylate in 15 ml of dichloromethane, and subsequently stirred for 24 hours at 0°. The reaction mixture is introduced into 140 ml of isopropanol, whereby the title compound precipitates. The deposit is filtered off, washed with isopropanol and dried. 2.1 g of the title compound are obtained as a slightly yellowish-coloured product. M.p.: from 150° (decomp.).

H$^1$-NMR (90 MHz; DMSO-d$_6$): 9.65 (1H, d, —N—H—, J=8 Hz); 9.36, 8.56, 8.10 (3H, pyridinium-H); 7.70 (1H, pyrazolyl-H); 6.43 (1H, pyrazolyl-H); 5.79 (1H, dd, H$_7$, J=8 Hz, J=5 Hz); 5.51 (2H, =C—C$\underline{H}_2$-pyridine); 5.12 (1H, d, H$_6$, J=5 Hz); 4.78 (2H, S, O—C$\underline{H}_2$—C=O); 4.11 (2H, q, O—C$\underline{H}_2$-CH$_3$, J=7 Hz); 3.45 (2H, H$_2$ and H$_2$'); 1.20 (3H, t, C$\underline{H}_3$—CH$_2$—, J=7 Hz).

EXAMPLE 15

(6R,7R)-7-[[(Z)-2-(ethoxycarbonylmethoxy)imino-2-(1H-pyrazol-3-yl)]acetamido]-3-[(1H-1,2,3-triazol-5-yl)thio-methyl]ceph-3-em-4-carboxylic acid:

1.5 ml of bis-(trimethylsilyl)acetamide are added to 1.6 g of (6R,7R)-7-amino-3-[(1H-triazol-5-yl)thiomethyl]ceph-3-em-4-carboxylic acid in 15 ml of dichloromethane. Stirring is then effected at 35°–40° until a clear solution is obtained. The solution is cooled to –5°. Then, 2.1 g of (Z)-2-[(ethoxy-carbonylmethoxy)imino]-2-(1H-pyrazol-3-yl)thioacetic-acid-S-benzothiazol-2-ylester are added, and stirring continues for 16 hours at 0°. 2 ml of isopropanol are added to the reaction solution, which is subsequently introduced into 150 ml of diisopropylether, whereby the title compound precipitates. The deposit is filtered off, washed with diisopropylether and dried. 2.1 g of the title compound are obtained as a slightly yellowish-coloured product. M.p.: from 170° (decomp.).

H$^1$-NMR (90 Mhz; DMSO-d$_6$); 9.50 (1H, d, —N—H—, 8 Hz ); 7.92 (1H, s, triazolyl-$\underline{H}$); 7.75 (1H, pyrazolyl-$\underline{H}$); 6.51 (1H, pyrazolyl-$\underline{H}$); 5.81 (1H, dd, H$_7$, J=8 Hz, J=5 Hz); 5.15 (1H, d, H$_6$, J=5 Hz); 4.71 (2H, s, O—CH$_2$—C=O); 4.20 (2H, q, O—C$\underline{H}_2$—CH$_3$, J=7 Hz); 4.15 3.43 (4H, =C—CH$_2$—S-triazole, H$_2$ and H$_2$'); 1.23 (3H, t, C$\underline{H}_3$—CH$_2$—, J=7 Hz).

EXAMPLE 16

(6R,7R)-7-[[(Z)-2-(1-ethoxycarbonylmethoxy)imino-2-(1H-pyrazol-3-yl)]acetamido]-3-[1-methyl-1H-tetrazol-5-yl)thio-methyl]ceph-3-em-4-carboxylic acid:

6.5 ml of bis(trimethylsilyl)acetamide are added to a suspension of 8.1 g of (6R,7R)-7-amino-3-[1-methyl-1H-tetrazol-5-yl)thio-methyl]ceph-3-em-4-carboxylic acid in 63 ml of dichloromethane. Stirring is effected at 20°–25° until a clear solution is obtained. The reaction solution is cooled to –10°, and then 9.6 g of (Z)-2-[(1-ethoxycarbonyl-methoxy)imino]-2-(1H-pyrazol-3-yl)thioacetic-acid-S-benzothiazol-2-ylester are added. After stirring for 16 hours at 0°, the reaction mixture is extracted with a solution of 75 ml of cold water and 31 ml of saturated sodium hydrogen carbonate solution. The aqueous phase is extracted with 10 ml of dichloromethane, then covered with a mixture of 16 ml of tetrahydrofuran and 64 ml of ethyl acetate, and acidified up to a pH of 2 whilst stirring with semi-concentrated hydrochloric acid. The phases are separated, and the aqueous phase is re-extracted with a mixture of 4 ml of tetrahydrofuran and 16 ml of ethyl acetate. The combined organic phases are washed with saturated sodium chloride solution, dried over sodium sulphate and then concentrated by evaporation under vacuum at 30°–35°. The remaining oil is dissolved in 15 ml of dichloromethane, and 190 ml of isopropanol are added in drops whilst stirring. After stirring for 24 hours at 20°, the deposit is filtered off by suction, washed with isopropanol and dried. 9.2 g of the title compound are obtained.

H$^1$-NMR (90 MHz; D$_2$O/K$_2$CO$_3$): 7.76 (1H, pyrazolyl-$\underline{H}$); 6.69 (1H, pyrazolyl-$\underline{H}$); 5.84 (1H, H$_7$, J=5 Hz); 5.19 (1H, H$_6$, J=5 Hz); 4.80 (2H, s, O—C$\underline{H}_2$—C=O); 4.21 (2H, q, O—C$\underline{H}_2$—CH$_3$, J=7 Hz); 4.19 (2H, =C—C$\underline{H}_2$-S-tetrazole); 4.01 (3H, S, C$\underline{H}_3$-tetrazole); 3.60 (2H, H$_2$ and H$_2$'); 1.20 (3H, t, C$\underline{H}_3$—CH$_2$—, J=7 Hz).

EXAMPLE 17

(6R,7R)-7-[[2-(2-amino-4-thiazolyl)-(Z)-2-(1-ethoxycarbonylethoxy)imino]acetamido]-3-(1-pyridiniummethyl)ceph-3-em-4-carboxylic acid. Chloride. Hydrochloride 4.7 g of bis-(benzothiazol-2-yl)disulphide are added to 3.3 g of 2-(2-amino-4-thiazolyl)-(Z)-2-[(1-ethoxycarbon-ylethoxy)imino]acetic acid and 3.7 g of triphenylphosphine in 40 ml of dichloromethane, and stirring is effected for 1 hour at 0°. After adding 3.3 g of (6R,7R)-7-amino-3-(1-pyridiniummethyl)ceph-3 -em-4-carboxylic acid. chloride, a solution of 1.8 ml of triethylamine in 20 ml of dichloromethane is added in drops at 0° with further stirring Over the course of 30 minutes. Stirring continues for 14 hours at 0° . The reaction mixture is introduced into a solution of 2.5 ml of concentrated hydrochloric acid in 300 ml of isopropanol, whereby the title compound precipitates. It is cooled and stirred for one hour at 0°. The deposit is filtered off, washed with isopropanol and dried. 5.1 g of the title compound are obtained as a slightly yellowish-coloured product. M.p.: from 150° (decomp.).

H$^1$-NMR (90 MHz, DMSO-d$_6$); 9.89 (1H, d, —N—$\underline{H}$;, J=8 Hz); 9.23, 8.73 and 8.27 (5H, pyridinium-$\underline{H}$); 7.04 (1H, s, thiazolyl-$\underline{H}$); 5.89 (1H, dd, H$_7$, J=8 Hz, J=5 Hz); 5.74 (2H, =C—CH$_2$-pyridine); 532 (1H, d, H$_6$, J=5 Hz); 4.80 (1H, q O—C$\underline{H}$—CH$_3$, J=7 Hz); 4.22 (2H, q, O—C$\underline{H}_2$—CH$_3$, J=7 Hz); 3.66 (2H, H$_2$ and H$_2$'); 1.21 (3H, d, C$\underline{H}_3$—CH—, J=7 Hz); 1.05 (3H, t, C$\underline{H}_3$—CH$_2$—, J=7 Hz).

EXAMPLE 18

7-[[(2-amino-4-thiazolyl)-2-oxoacetyl]amino]-3-[[(1-methyl-1H-tetrazol-5-yl)thio]methyl]-8-oxo-5-thia-1-aza-bicyclo[4.2.0]oct-2-en-2-carboxylic acid 3.29 g of 7-amino-3-[(1-methyl-1H-tetrazol-5-yl)thiomethyl]ceph-3-em-4-carboxylic acid are suspended in 25 ml of dichloromethane and mixed with 2.7 ml of N,O-bis-(trimethylsilyl)acetamide. After 15 minutes, a clear solution is present. This is cooled to –15°, and 3.9 g of 2-(2-aminothiazol-4-yl)-2 -oxothioacetic-acid-S-benzothiazol-2-ylester are added. After stirring for four hours at –15°, the preparation is stirred into 100 ml of ethanol, whereby the end product precipitates. This is stirred for one hour at 0°, filtered, washed with ethanol and vacuum dried. Yield: 3.9 g, i.e. 80.7%. M.p.: from 145° (decomp.).

IR: 3350 N—H, 1800 C=O (β-lactam), 1690 C=O (amide), 1545 (amide

EXAMPLE 19

7-[[(2-amino-4-thiazolyl)-2-oxoacetyl]amino]-3-(1-pyridinium)-methyl-8-oxo-5-thia-1-azabicyclo[4.2.0]oct-2-en-2-carboxylic acid. Chloride 3.28 g of 7-amino-3-(1-pyridiniummethyl)ceph-3-em-4-carboxylic-acid. chloride are suspended in 25 ml of dichloromethane, and mixed with 3 ml of N,O-bis-(trimethylsilyl) acetamide. After 10 minutes, a clear solution is present. This is cooled to –15°, and 3.9 g of 2-(2-aminothiazol-4-yl)-2- oxothioacetic-acid-S-benzothiazol-2-ylester are added. After stirring for four hours at −15°, the preparation is stirred into 100 ml of ethanol, whereby the end product precipitates. This is stirred for one hour at 0°, filtered, washed with ethanol and vacuum dried. Yield: 4.0 g, i.e. 83.0%. M.p.: from 162° (decomp.).

IR: NH 3300 (wide), 1765, C=O (β-lactam), 1645, C=O (amide), 1610, (amide II).

EXAMPLE 20

7-[[(2-amino-4-thiazolyl)-2-oxoacetyl]amino]-3-acetoxymethylceph-3-em-4-carboxylic acid 5.44 g of 7-amino-3-acetoxymethylceph-3-em-4-carboxylic acid are suspended under a nitrogen atmosphere in 50 ml of dry di-chloromethane, and mixed with 5.4 ml of N,O-bis(trimethylsilyl)acetamide. The preparation is stirred at room temperature until a clear solution is present, and then cooled to −15°. 8.4 g of 2-(2-amino-4-thiazolyl)-2-oxothioacetic-acid-S-benzothiazol-2-ylester are added, and stirred for two hours at −15° and then for two hours at 0°. The solvent is carefully drawn off in a rotary evaporator, and the oily residue is rubbed with 50 ml of ethanol, whereby the title compound precipitates. 6.3 g are obtained in the form of a yellow powder.

IR: 3335 NH, 1800 c=o (β-lactam), 1755 c=o, 1685 c=o (amide I) 1515 (amide II)

EXAMPLE 21

7-[[(2-amino-4-thiazolyl)-2-oxoacetyl]amino]-3-methylceph-3-em-4-carboxylic acid 4.28 g of 7-amino-3-methylceph-3-em-4-carboxylic acid are suspended under a nitrogen atmosphere in 80 ml of dry dichloromethane, and mixed with 5.4 ml of N,O-bis(trimethylsilyl)acetamide. The preparation is stirred at room temperature until a clear solution is present, and then cooled to −15°. 8.4 g of 2-(2-amino-4-thiazolyl)-2-oxothioacetic-acid-S-benzothiazol- 2-ylester are added, and stirred for one hour at −15°, one hour at 0° and then two hours at +20°. The solvent is carefully drawn off on a rotary evaporator, and the oily residue is rubbed with 50 ml of ethanol. The resultant deposit is filtered, washed with ethanol and ether, and vacuum dried at 40°. 5.3 g of the title compound are obtained as a yellow powder.

IR: 3340 NH, 1790 c=o (β-lactam), 1685 c=o, 1540 (amide II).

EXAMPLE 22

7-[[(2-amino-4-thiazolyl)-2-oxoacetyl]amino]-3-(1,2,3-triazol-5-ylthiomethyl)ceph-3-em-4-carboxylic acid 6.26 g of 7-amino-2-(1,2,3-triazol-5-ylthiomethyl)ceph-3-em-4-carboxylic acid are converted into the silyl ester in 50 ml of dichloromethane by adding 5.4 ml of N,O-bis(trimethylsilyl)acetamide. The mixture is cooled to −15°, and 10.1 g of 2-(2-amino-4-thiazolyl)-2-oxothioacetic-acid-S-benzothiazol-2-ylester are added in the form of the tetrahydrofuran solvate. After two hours at −15° and one hour at 0°, the dichloromethane is removed in a rotary evaporator, and the residue is mixed with 100 ml of methanol. The deposit is isolated in known manner. 8.4 g of the title compound are obtained as a yellow powder.

IR: 3320 NH (wide), 1790 c=o (β-lactam, 1680 c=o, 1530 (amide I)

EXAMPLE 23

7-[[(2-amino-4-thiazolyl)-2-oxoacetyl]amino]-3-[(2,3-cyclopenteno-1-pyridinium)methyl]ceph-3-em-4-carboxylate 9.88 g of 7-amino-3-[(2,3-cyclopenteno-1-pyridinium)methyl]-ceph-3-em-4-carboxylate. hydroiodide. monohydrate are silylated in 100 ml of dichloromethane with 11.4 ml of N,O-bis(trimethylsilyl)acetamide. The resultant solution is cooled to −15°, and mixed with 8.4 g of 2-(2-amino-4-thiazolyl)-2 -oxothioacetic-acid-S-benzothiazol-2-ylester. The solution is stirred for three hours at −15° and then 100 ml of ethanol and 3 ml of triethylamine are added. The preparation is stirred for one hour at 0°, the resultant deposit filtered off, washed and dried. 11.5 g of the title compound are obtained as an orange powder.

IR: 3300 NH, 2965 CH$_2$, 1795 c=o (β-lactam), 1690 c=o, 1635 (amide I), 1545 (amide II).

EXAMPLE 24

7-[[(2-amino-4-thiazolyl)-2-oxoacetyl]amino]-3-[(2,5-dihydro-6-hydroxy-2-methyl-5-oxo-1,2,4-triazin-3-yl)thiomethyl]ceph-3-em-4-carboxylic acid 14.85 ml of N,O-bis(trimethylsilyl)acetamide are added at 30° to 7.4 g of 7-amino-3-[(2,5-dihydro-6-hydroxy-2-methyl-5-oxo-1,2,4 -triazin-3-yl)thiomethyl]ceph-3-em-4-carboxylic acid (water content: 3.7%) in 50 ml of dichloromethane. After two hours at 30°, the mixture is cooled to −15°. 8.1 g of 2-(2-amino-4-thiazolyl)-2-oxothioacetic-acid-S-benzothiazol-2-ylester are added, and stirred for six hours at −15°. The preparation is added to 500 ml of ethanol which has been warmed to 50°, then cooled whilst stirring and stirred for one hour at 0°. The deposit is filtered off, washed and dried. 9.1 g of the title compound are obtained as a yellow powder. IR: 3320 NH, 1805 c=o, 1735 c=o, 1690 c=o, 1645 (amide I), 1555 (amide II).

EXAMPLE 25

2-(2-amino-4-thiazolyl)-(Z)-2-[(1-diphenylmethoxycarbonyl-1-methylethoxy)imino]acetic acid 245 g of O-(1-diphenylmethoxycarbonyl-1-methylethyl)hydroxylamine and 148 g of (2-amino-4-thiazolyl)glyoxylic acid are stirred for 4 days at room temperature in 1700 ml of ethanol. The crystalline deposit is filtered off by suction and washed with ethanol. After recrystallisation from methanol, 265 g (70%) of the title compound are obtained. M.p.: 135°.

H$^1$-NMR 90 MHz, DMSO-d$_6$): 7.22 (1OH, m, phenyl); 6.65 (1H, s, thiazole); 6.60 (1H, s, Ph$_2$CH); 1.38 (6H, s, C(CH$_3$)$_2$).

EXAMPLE 26

2-(2-amino-4-thiazolyl)-(Z)-2-[(1-diphenylmethoxycarbonyl-1-methylethoxy)imino]acetic acid:

21.5 g of O-(1-diphenylmethoxycarbonyl-1-methylethyl)hydroxylamine and 12 g of (2-amino-4-thiazolyl)glyoxylic acid are refluxed for 3 hours in 1500 ml of methanol. The cloudy reaction mixture is filtered whilst hot, and then stirred for 12 hours at 10°. The resultant crystalline deposit is filtered off by suction and washed with methanol. 24 g (80%) of the title compound are obtained.

EXAMPLE 27

2-(2-amino-4-thiazolyl)-(Z)-2-[(1-diphenylmethoxycarbonyl-1-methylethoxy)imino]acetic acid 135 g of (2-amino-4-thiazolyl)glyoxylic acid are added whilst cooling with ice to a solution of 245 g of O-(1-diphenylmethoxycarbonyl- 1-methylethyl)-hydroxylamine in 400 ml of dimethylformamide. The solution is stirred for 5 hours without cooling, and is then added to 4 l of methanol. In order to complete precipitation, stirring continues for 5 hours at 10°, and the product is then filtered off by suction and dried. 320 g (93%) of the title-compound are obtained as colourless crystals.

EXAMPLE 28

2-(2-amino-4-thiazolyl)-(Z)-2-[(diphenylmethoxycarbonylmethoxy)imino]acetic acid 16.5 g of O-diphenylmethoxycarbonylmethylhydroxylamine and 9.9 g of (2-amino-4-thiazolyl)glyoxylic acid are stirred for 3 hours at room temperature in 30 ml of dimethylformamide. The reaction mixture is introduced into 500 ml of methanol, and the resultant deposit is filtered off. 18 g of the title compound are obtained as colourless crystals. M.p.: 125°.

$H^1$-NMR (90 Hz, DMSO-$d_6$): 7.37 (10H, m, phenyl); 6.97 (1H, s, thiazole); 6.88 (1H, s, Ph$_2$C$\underline{H}$); 4.91 (2H, s, O—C$\underline{H}_2$).

EXAMPLE 29

2-(2-amino-4-thiazolyl-(Z)-2-[(1-ethoxycarbonylethoxy)imino]acetic acid 17.2 g of (2-amino-4-thiazolyl)glyoxylic acid are added whilst cooling with ice to a solution of 14.6 g of O-(1-ethoxycarbonylethyl)hydroxylamine in 20 ml of dimethylformamide. The solution is stirred for 12 hours without cooling, and then diluted with 180 ml of methanol. In order to complete crystallisation, stirring continues for 5 hours at −5°, and then the product is filtered off by suction and dried. 24.7 g (86%) of the title compound are obtained. M.p.: 166°.

EXAMPLE 30

2-(2-amino-4-thiazolyl)-(Z)-2-(1-diphenylmethoxycarbonylpropoxyimino)acetic acid 30 g of O-(1-diphenylmethoxycarbonylpropyl)hydroxylamine and 16.2 g of (2-amino-4-thiazolyl)glyoxylic acid are stirred for 1 hour at room temperature in 60 ml of dimethylformamide. The reaction mixture is diluted with dichloromethane, and washed with 2N hydrochloric acid and several times with water. After evaporating the dichloromethane phase, 41 g of the title compound remain as a solid residue.

EXAMPLE 31

2-(2-amino-4-thiazolyl)-(Z)-2-[(1-diphenylmethoxycarbonyl-1-methylethoxy)imino]thioacetic-acid-S-benzothiazol-2-ylester 50 g of 2-(2-amino-4-thiazolyl)-(Z)-2-[(1-diphenylmethoxycarbonyl- 1-methylethoxy)imino]acetic acid, 37 g of triphenylphosphine and 47 g of bis-(benzothiazol-2-yl)disulphide in 400 ml of dichloromethane are stirred for 3 hours at room temperature. Then, the dichloromethane is distilled off and the oily residue is taken up in 300 ml of methanol. After crystal formation, stirring is effected for 5 hours whilst cooling with ice, the deposit is filtered off by suction, washed with methanol and dried. 43 g (65%) of the title compound are obtained as a yellow product. M.p.: 110°.

$H^1$-NMR (90 MHz, DMSO-$d_6$): 7.97 and 7.48 (4H, benzothiazolyl); 7.22 (10H, m, phenyl), 6.88 (1H, s, thiazolyl); 6.60 (1H, s, Ph$_2$C$\underline{H}$), 1.63 (6H, s, C(C$\underline{H}_3$)$_2$).

EXAMPLE 32

2-(2-amino-4-thiazolyl)-(Z)-2-[(1-diphenylmethoxycarbonyl-1-1-methylethoxy)imino]thioacetic-acid-S-benzothiazol-2-ylester 50 g of 2-(2-amino-4-thiazole)-(Z)-2-[(1-diphenylmethoxycarbonyl-1-methylethoxy)imino]acetic acid and 37 g of triphenylphosphine are boiled for 1 hour in a water separator in 400 ml of dichloromethane The resultant suspension is cooled to 0°, and mixed with 40 g of bis-(benzothiazol-2-yl)disulphide. Stirring is effected for 30 minutes at 0°, and then the dichloromethane is distilled off. The oily residue is taken up in 450 ml of ethanol of 0°, and the resultant suspension is stirred over night at 0°. After filtration, washing with methanol and drying at room temperature in a vacuum, 51 g (75%) of the title compound are obtained as a yellow powder.

EXAMPLE 33

2-(2-amino-4-thiazolyl)-(Z)-2-[(diphenylmethoxycarbonylmethoxy)imino]thioacetic-acid-S-benzothiazol-2-ylester 2.1 g of 2-(2-amino-4-thiazolyl)-(Z)-2-[(diphenylmethoxycarbonylmethoxy)imino]acetic acid, 1.7 g of triphenylphosphine and 2.2 g of bis-(benzothiazol-2-yl)disulphide are stirred for 2 hours at 0° in 50 ml of dichloromethane. The dichloromethane is then distilled off and the solid residue is digested with methanol. 2.6 g of the title compound are obtained as a colourless powder. M.p.: 152°.

$H^1$-NMR (90 MHz, DMSO-$d_6$): 8.11 and 7.59 (4H, benzothiazolyl); 7.33 (10H, m, phenyl); 7.03 (1H, s, thiazole); 6.92 (1H, s, Ph$_2$C$\underline{H}$); 5.03 (2H, s, O—C$\underline{H}_2$).

EXAMPLE 34

2-(2-amino-4-thiazolyl)-(Z)-2-[(1-ethoxycarbonylethoxy)imino]thioacetic-acid-S-benzothiazol-2-ylester 5.1 g of 2-(2-amino-4-thiazole-(Z)-2-[(1-ethoxycarbonylethoxy)imino]acetic acid and 5.6 g of triphenylphosphine are boiled for 1 hour in a water separator in 40 ml of dichloromethane. The resultant suspension is cooled to 0° and mixed with 6.7 g of bis-(benzothiazol-2-yl)disulphide. Stirring is effected for 1 hour at 0°, and then the dichloromethane is distilled off. The oily residue is taken up in 40 ml of methanol, and stirred over night at 0°. The deposit is filtered off, washed with methanol and dried. 5.5 g (70%) of the title compound are obtained as a slightly yellow-coloured product. M.p.: 113°.

H$^1$-NMR (90 MHz; CDCl$_3$): 7.99 and 7.47 (4H, benzothiazolyl-H); 6.81 (1H, s, thiazolyl-H); 4.81 (1H, q, O—CH—CH$_3$, J=7 Hz); 4.21 (2H, q, O—CH$_2$—CH$_3$, J=7 Hz); 1.51 (3H, d, CH$_3$—CH—, J= 7 Hz); 1.29 (3H, t, CH$_3$—CH$_2$—, J=7 Hz).

EXAMPLE 35

(Z)-2-[(1-ethoxycarbonylmethoxy)imino]-2-(1 H-pyrazol-3-yl)thioacetic-acid-S-benzothiazol-2-ylester 41.5 g of bis-(benzothiazol-2-yl)disulphide are added to a solution of 32.7 g of triphenylphosphine in a mixture of 200 ml of 1,1,1-trichloroethane and 40 ml of acetone. The suspension is stirred for 2 hours. Then, 24.1 g of (Z)-2-[(1-ethoxycarbonylmethoxy)imino]-2-(1H-pyrazol-3-yl)-acetic acid are added at 0°, and stirring is effected for 2 hours at 0°. The deposit is filtered off, washed with 1,1,1-trichloroethane and dried. 29.4 g of the title compound are obtained as a slightly yellowish-coloured product. M.p.: 112°–114°.

H$^1$-NMR (90 MHz; CDCl$_3$): 8.00 (2H, benzothiazolyl-H); 7.52 (3H, benzothiazolyl-H, pyrazolyl-H); 6.50 (1H, pyrazolyl-H); 4.78 (2H, s, O—CH$_2$—C=O); 4.23 (2H, q, O—CH$_2$— CH$_3$, J=7 Hz); 1.28 (3H, t, CH$_3$—CH$_2$—, J=7 Hz).

EXAMPLE 36

2-(2-aminothiazol-4-yl)-2-oxothioacetic-acid-S-benzothiazol-2-ylester 34.4 g of aminothiazolylglyoxylic acid are suspended in 500 ml of dichloromethane, and mixed whilst stirring with 28 ml of triethylamine. The mixture is cooled to −15°, and 64 g of triphenylphosphine and 80 g of bisbenzothiazol-2-yl-disulphide are added. After stirring for two hours at −15°, the orange deposit is filtered off, washed with cold dichloromethane and vacuum dried. Yield: 57.7 g, i.e. 89.8%.

IR: 3300 N-H, 1675 carbonyl (thioester), 1645 carbonyl (amide), 1540 amide bands.

EXAMPLE 37

2-(2-aminothiazol-4-yl)-2-oxothioacetic-acid-S-benzothiazol-2-ylester 80 g of bisbenzothiazol-2-yl-disulphide and 64 g of triphenylphosphine are suspended in 500 ml of tetrahydrofuran and cooled to −15°. 34.4 g of aminothiazolylglyoxylic acid are added, and 16.1 g of pyridine are added slowly in drops, such that the internal temperature does not exceed −15°. The orange suspension is stirred for two hours at −15°. The deposit is filtered off, washed with cold tetrahydrofuran and vacuum dried. Yield: 62.2 g as tetrahydrofuran solvate. M.p.: at 80° escape of THF, from 123° (decomp.). THF content (by gas-chromatography): 17%.

We claim:
1. A compound of formula IVe

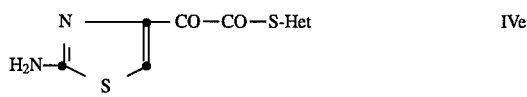

IVe where Het is 2-pyridyl or 2-benzothiazolyl.

2. The compound according to claim 1, which is 2-(2-aminothiazol-4-yl)-2-oxothioacetic acid, S-benzothiazol-2-yl ester.

* * * * *

UNITED STATES PATENT AND TRADEMARK OFFICE
CERTIFICATE OF CORRECTION

PATENT NO. : 5,484,928
DATED : Jan. 16, 1996
INVENTOR(S) : Hubert Sturm, Landeck; Heinrich Thaler, Kirchbichl; Werner Veit, Kufstein, all of Austria It is certified that error appears in the above-indentified patent and that said Letters Patent is hereby corrected as shown below:

Title page, left hand column, line 2.
"Sturm et al." should read -- Ascher et al. -- .

Title page, left hand column, lines 5 to 7,
"Inventors: Hubert Sturm, Landeck; Heinrich Thaler, Kirchbichl; Werner Veit, Kufstein, all of Austria"

should read -- Inventors: Gerd Ascher, Kundl; Hubert Sturm, Landeck; Heinrich Thaler, Kirchbichl; Werner Veit, Kufstein, all of Austria. --

Signed and Sealed this

Twenty-ninth Day of October 1996

Attest:

BRUCE LEHMAN

*Attesting Officer*     *Commissioner of Patents and Trademarks*